(12) United States Patent
Zhao et al.

(10) Patent No.: US 6,668,688 B2
(45) Date of Patent: Dec. 30, 2003

(54) EXPANDABLE SCREW APPARATUS AND METHOD THEREOF

(76) Inventors: Chunfeng Zhao, 2130 9th Ave. NE., Rochester, MN (US) 55906; Bradford L. Currier, 2005 Nerrihills Dr. SW., Rochester, MN (US) 55902; Kai-Nan An, 685 Itasca Ct., Rochester, MN (US) 55901; Fredrick Schultz, 2446 Northern Hill Ct. NE., Rochester, MN (US) 55906; Patricia Neale, 520 Zumbro Dr. NW., Rochester, MN (US) 55901

( * ) Notice: Subject to any disclaimer, the term of this patent is extended or adjusted under 35 U.S.C. 154(b) by 0 days.

(21) Appl. No.: 09/893,818

(22) Filed: Jun. 28, 2001

(65) Prior Publication Data

US 2003/0000350 A1 Jan. 2, 2003

(51) Int. Cl.[7] ................................. B25B 23/00
(52) U.S. Cl. ............................ 81/439; 606/73; 81/55; 411/51
(58) Field of Search .................... 606/61, 63, 65, 606/71, 72, 73; 411/44, 51, 72; 81/13, 55, 58.1, 437, 439

(56) References Cited

U.S. PATENT DOCUMENTS

| | | | |
|---|---|---|---|
| 1,677,473 A | * | 7/1928 | Gast ................................. 81/55 |
| 3,889,558 A | * | 6/1975 | Duncan ........................... 81/55 |
| RE28,841 E | | 6/1976 | Allgower et al. |
| 4,229,999 A | * | 10/1980 | Rottigni ....................... 81/9.24 |
| 4,359,906 A | | 11/1982 | Cordey |
| 4,388,921 A | | 6/1983 | Sutter et al. |
| 4,513,744 A | | 4/1985 | Klaue |
| 4,522,090 A | * | 6/1985 | Kittle ............................. 81/55 |
| 4,887,596 A | | 12/1989 | Sherman |
| 5,209,753 A | | 5/1993 | Biedermann et al. |
| 5,343,784 A | * | 9/1994 | Neuhaus ........................ 81/55 |
| 5,702,216 A | * | 12/1997 | Wu ............................. 411/32 |
| 5,810,823 A | | 9/1998 | Klaue et al. |
| 5,976,141 A | | 11/1999 | Haag et al. |
| 6,063,090 A | | 5/2000 | Schläpfer |
| 2001/0045144 A1 | * | 11/2001 | McClure ........................ 81/58 |

OTHER PUBLICATIONS

Lesoin, et al., "Expanding Bolt for Anterior Cervical Spine Osteosynthesis: Technical Note", Neurosurgery, vol. 12, No. 4, pp. 458–459, 1993, Congress of Neurological Surgeons.
Cook, et al., "Biomechanical Evaluation and Preliminary Clinical Experience with and Expansive Pedicle Screw Design", Journal of Spinal Disorders, vol. 13, No. 3, pp. 230–236, 2000, Lippincott Williams & Wilkings, Inc.

* cited by examiner

Primary Examiner—James G. Smith
(74) Attorney, Agent, or Firm—Merchant & Gould P.C.

(57) ABSTRACT

An apparatus for an expandable screw including an outer screw, a inner screw, and an end nut. An assembly and method for driving and expanding an expandable screw apparatus into a surface or structure. The assembly and method dynamically expand the expandable screw by driving and expanding the expandable screw simultaneously.

23 Claims, 8 Drawing Sheets

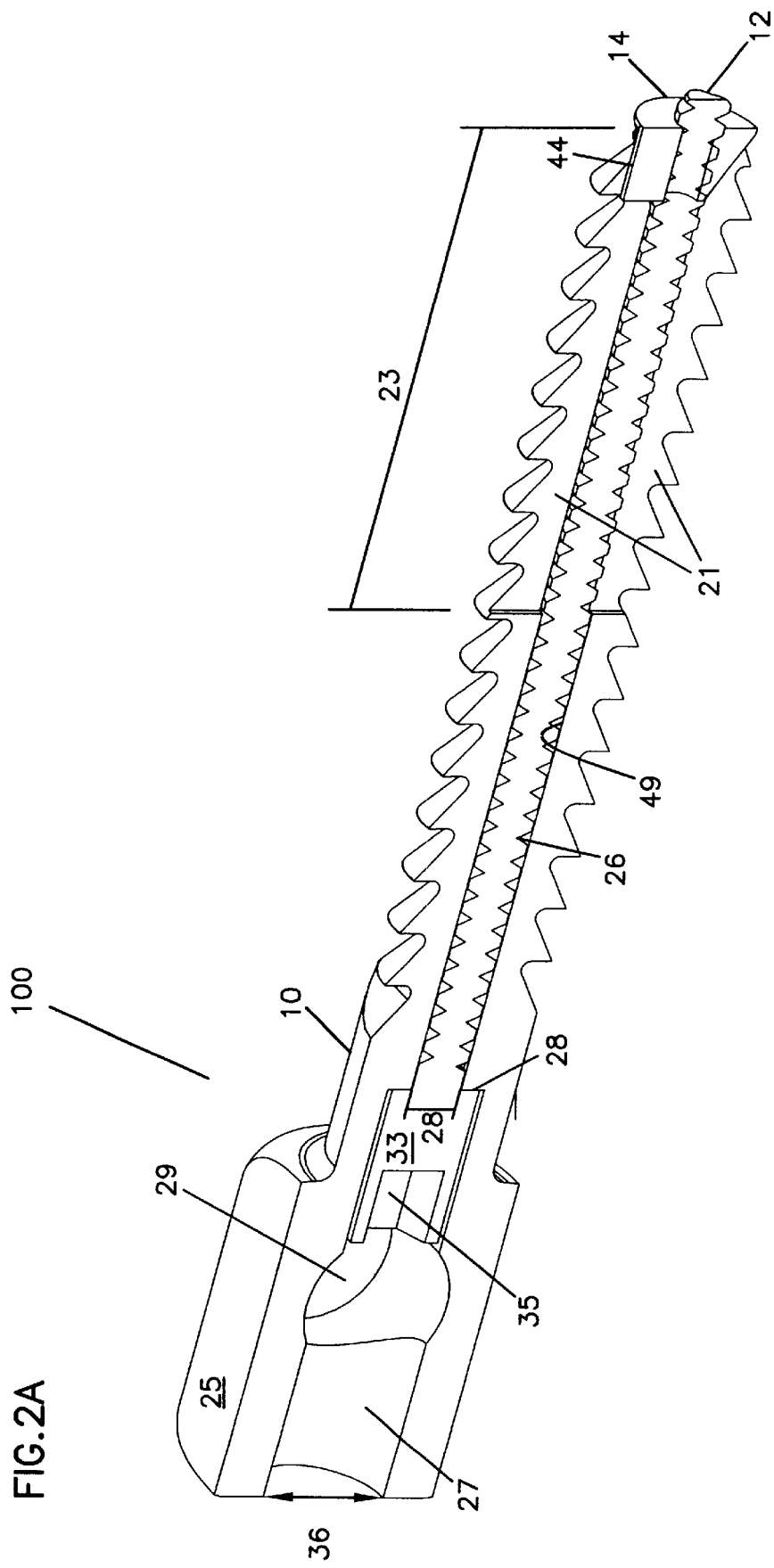

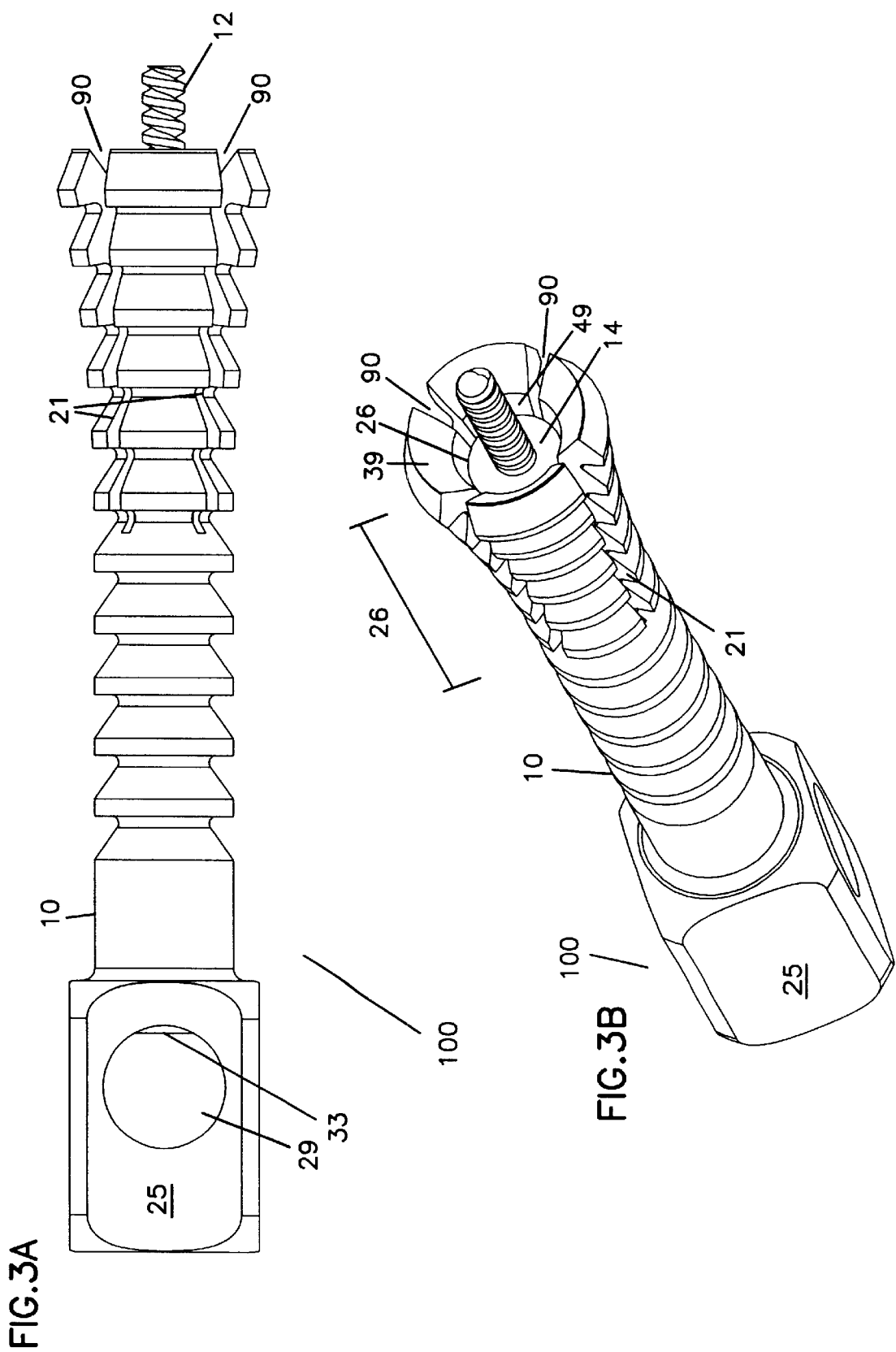

EXPANDABLE SCREW APPARATUS AND METHOD THEREOF

FIELD OF THE INVENTION

The present invention relates to expandable screws, and more particularly, to an expandable screw apparatus and method for driving and expanding the same in a structure. In addition, the present invention relates to an assembly for the same.

BACKGROUND OF THE INVENTION

Screw fixation is commonly used in spinal internal posterior fixation surgeries for various spinal disorders such as spondylolisthesis, trauma, tumors, deformities and other conditions. Many screw fixation systems have been developed and are used increasingly to connect different designs of such screws to structural members such as plates, rods, bars, and the like. In these systems, pedicle screws are often employed, which are cancellous bone screws that can sustain high loads. The strength of the bone-screw interface is crucial, because the interface must be strong enough to withstand the correcting forces applied intraoperatively and stable enough to avoid deformation under physiologic loading after surgery. A poor bone-screw interface can decrease the strength and stability of the construct and cause pseudoarthrosis, loss of correction, and failure of surgeries due to screw loosening or pullout, for instance, in an osteoporotic patient. The bone-screw interface is affected by variables such as bone mineral density (BMD), screw design, insertion technique, and supplementary instruments. Particularly, the BMD has a critical influence on the bone-screw interface. However, host bone quality mostly is beyond a surgeon's control. Therefore, increasing the strength of the bone-screw interface by focusing on screw design and screw hole preparation continues to be an important aspect of study in screw fixation systems.

Various systems have been implemented for fixating screws into structures such as bone. For instance, simple pedicle screws that did not expand were driven into bone in the past. However, this type of screw did not optimize holding power and therefore the bone-screw interface strength lacked. In addition, supplemental devices have been used to augment the holding strength of fixation devices. For example, polymethylmethacrylate (PMMA) has been employed as an injection cement to increase holding power of fixated screws. However, PMMA may lose its fixative strength over time and can cause neurological injury by extrusion of the cement. Therefore, it has not been used routinely. Also, supplemental devices have included laminar hooks in combination with pedicle screws and/or a washer or staple combined with vertebral screws. Furthermore, other devices such as an anchor have been used in combination with transvertebral screws. However, uses of these supplemental instruments are not ideal as they can require the recruitment of additional bone structures and can significantly increase the complexity of the fixation procedure, or they are not practical for fixation into particular structures, such as bone.

Still a more useful pedicle screw has been developed, wherein the screw is expandable at the driven end upon insertion into a bone structure or the like. However, as this screw is expanded after the formation of bone threads, the bone threads tend to compress thereby compromising the holding condition of the bone.

Accordingly, there remains a need for a means of increasing the strength of the structure-screw interface. Also, there is yet a need for a less complicated and more convenient way of fixating screws to a surface and/or structure.

SUMMARY OF THE INVENTION

In accordance with the present invention, the above and other problems were solved by providing an expandable screw apparatus and an expandable screw driving and expanding assembly, as well as a method for inserting and expanding an expandable screw.

In one embodiment of the present invention, an expandable screw apparatus includes an outer screw having a longitudinal hollow core and a plurality of longitudinal expandable slits proximate a distal end, and an inner screw, disposed inside the longitudinal hollow core of the outer screw, having a distal end extended outside the longitudinal hollow core of the outer screw. Further, the expandable screw apparatus includes an end nut, engaged with the distal end of the inner screw, wherein by rotating the outer screw relative to the inner screw while simultaneously holding the inner screw, the end nut is drawn into the hollow core of the outer screw, thereby causing simultaneous expansion of the expandable slits in a transversal direction.

Further in one embodiment of the present invention, a method is provided for fixation of an expandable screw apparatus into a structure. First, an expandable screw apparatus is provided, which includes an outer screw having a longitudinal hollow core, an inner screw, and a end nut. The expandable screw apparatus is driven a length inwards without expanding the screw apparatus. Then the end nut connected to the inner screw can be engaged into one of a plurality of longitudinal slits at a distal end of the outer screw by rotating the inner screw to draw the end nut inwards. After the end nut is engaged, the expandable screw apparatus can continue being driven inwards by simultaneously holding the inner screw in place to prevent the inner screw from rotating, and rotating and driving the outer screw thereby moving the end nut proximally into the longitudinal hollow core of the outer screw towards the proximal end of the inner screw, the end nut includes a portion having a larger diameter than a diameter of the longitudinal hollow core. By simultaneously rotating the outer screw of the expandable screw apparatus and holding the inner screw of the expandable screw apparatus, which prevents the inner screw from rotating, the expandable screw is being driven into a structure, while simultaneously being expanded in an outwardly transversal direction from the longitudinal hollow core at its longitudinal slits.

Yet in one embodiment in a method of fixating an expandable screw, the end nut can be pre-engaged into one of the longitudinal slits at the end of the outer screw, thereby eliminating the need for the step of engaging the end nut as described in the above embodiment.

Still in one embodiment, an assembly for driving and expanding an expandable screw apparatus, includes an outer screw, an inner screw, and an end nut as described in the above embodiment. In addition, the assembly contains a driver mechanism and an elongated stabilizing member. The driver mechanism contains a structural end connectable to a structural head of the outer screw, the driver mechanism also includes a hollow shaft. The elongated stabilizing member includes an end insertable first through the hollow shaft of the driver mechanism towards the proximal end of the outer screw and through the longitudinal hole region of the outer screw. The elongated stabilizing member is connectable to an insertion space of the proximal end cap of the inner screw. Furthermore, the elongated stabilizing member provides rotating means for the end nut to engage the longitudinal slits. Moreover, during dynamic expansion, the elongated stabilizing member provides holding means to prevent the inner screw from rotating.

One advantage of the present invention is that the employment of an expandable screw can increase the holding strength to the structure it is fixed to or therein. In addition, the method of the present invention allows an expandable screw to be inserted such that the strength of the structure-screw interface is improved, and also provides a less complicated way for inserting an expandable screw.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there are illustrated and described specific examples of an apparatus in accordance with the invention.

BRIEF DESCRIPTION OF THE DRAWINGS

Referring now to the drawings in which like reference numbers represent corresponding parts throughout:

FIG. 2A represents a cross-sectional view of the expandable screw apparatus of FIG. 1 showing an end nut before engagement with longitudinal slits of an outer screw of the expandable screw apparatus in accordance with the principles of the present invention.

FIG. 3A represents a perspective view of the expandable screw apparatus of FIG. 1 expanded in accordance with the principles of the present invention.

FIG. 3B represents a side view of the expandable screw apparatus of FIG. 1 expanded in accordance with the principles of the present invention.

DETAILED DESCRIPTION OF THE PREFERRED EMBODIMENT

In the following description of the illustrated embodiments, reference is made to the accompanying drawings that form a part hereof, and in which is shown by way of illustration of the embodiments in which the invention may be practiced. It is to be understood that other embodiments may be utilized as structural changes may be made without departing from the spirit and scope of the present invention.

The present invention provides an expandable screw apparatus for fixation into a structure.

Figure 1:
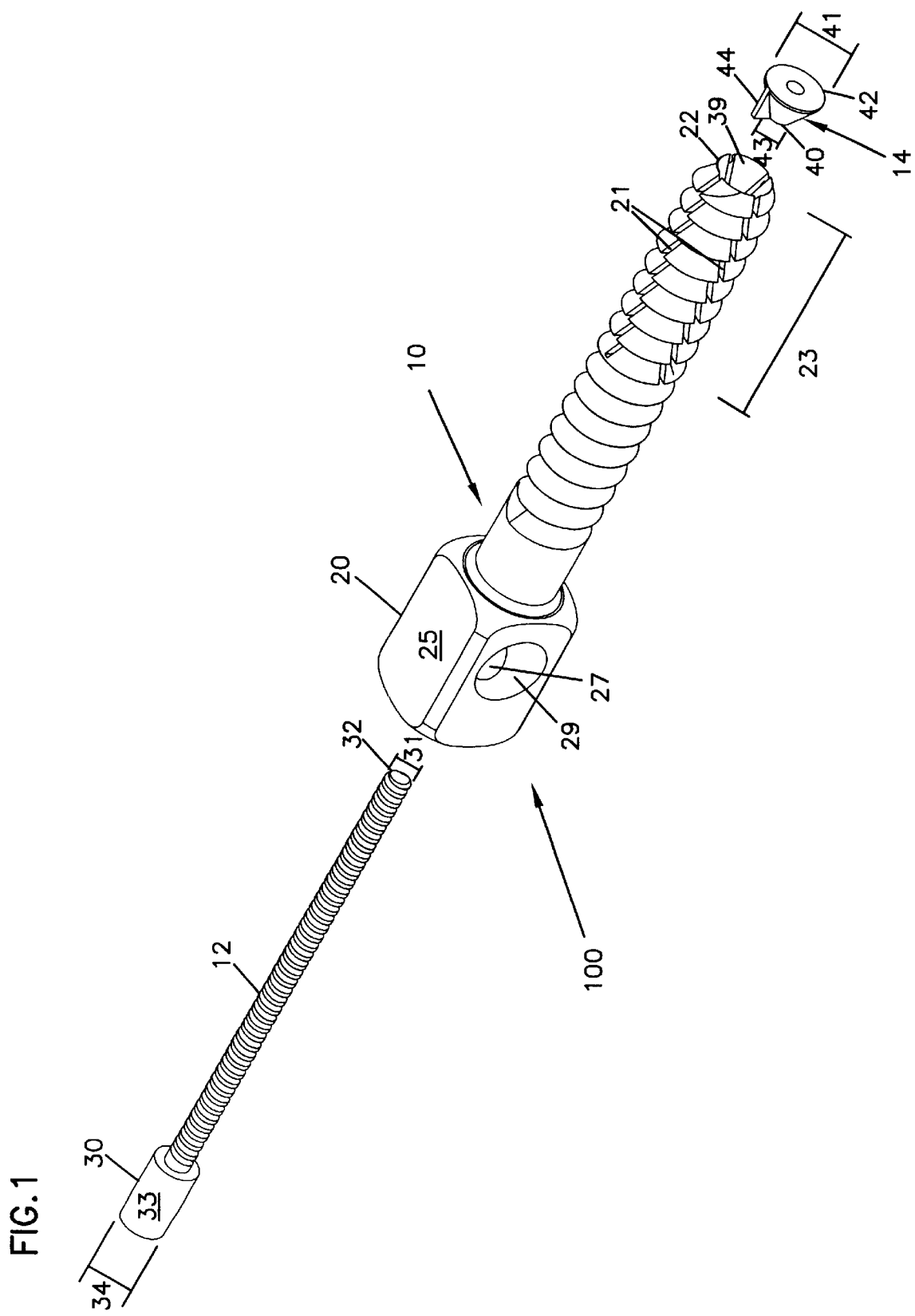
FIG. 1 represents an exploded view of one embodiment for an expandable screw apparatus in accordance with the principles of the present invention.

In FIGS. 1 and 2A–D, the expandable screw apparatus 100 includes a threaded outer screw 10, a threaded inner screw 12, and an end nut 14. The structure of the outer screw 10 is such that a longitudinal hollow core 26 runs through the center axis of the outer screw 10 from the a proximal end 20 to a distal driving end 22. The longitudinal hollow core 26 has a tapered portion 39 at the distal end 22 as best depicted in FIG. 1. The proximal end 20 is provided with a structural head 25 for attachment to a driver mechanism such as, but not limited to, a wrench. Further, the proximal end 20 has a longitudinal hole region 27, which a stop region 28 is located therein. A diameter 36 of the longitudinal hole region 27 is greater than a diameter 24 of the longitudinal hollow core 26, thereby creating the stop region 28 between the hole region 27 and the hollow core 26. Also in the proximal end 20, structural through holes 29 are provided in a transverse direction through and across the hollow region 27 as a means for supporting a structural frame such as, but not limited to, rods, plates, and bars. At the distal driving end 22 of the outer screw 10, a plurality of longitudinal slits 21 are provided wherein the slits 21 extend a length 23 from the distal end 22 towards the proximal end 20. The longitudinal slits 21 are disposed apart at every certain degrees, e.g. 90°. The longitudinal slits 21 have an inner surface 49 that is substantially smooth. The outer screw 10 has a thread having either a right handed orientation or a left handed orientation on its outer surface.

The structure of the threaded inner screw 12 has a proximal end 30 and a distal end 32. The proximal end 30 has a proximal end cap 33 wherein the proximal end cap 33 includes an insertion space 35 as best shown in FIG. 2A. A diameter 34 of the proximal end cap 33 is greater than a diameter 31 of a remaining portion of the inner screw 12. Typically, this remaining portion of the inner screw 12 is the threaded portion. In addition, the proximal end cap diameter 34 is less than the diameter 36 of the longitudinal hole region 27 of the outer screw 10 but greater than the diameter 24 of the longitudinal hollow core 26 of the outer screw 10. Furthermore, the diameter 31 of the remaining portion of the inner screw 12 is less than the diameters 34 and 36 of both the longitudinal hollow region 27 and longitudinal hollow core 26, respectively. According to the above diameters, the inner screw 12 is insertable through the hollow region 27 and the longitudinal hollow core 26 of the outer screw 10 from the proximal end 20 to the distal end 22. When the end cap 33 of the inner screw 12 contacts the stop region 28 of the outer screw 10, the inner screw 12 is stopped and can no longer continue movement towards the distal end 22 of the outer screw 10. The orientation of the thread of the inner screw 12 is opposite of the orientation of the thread of the outer screw 10. Meaning, if the outer screw 10 has a right handed thread on its outer surface, where the outer screw 10 is driven in clockwise, then the inner screw 12 will have a left handed thread on its outer surface, where the inner screw 12 is driven in counterclockwise, or vice versa.

The end nut 14 includes a lip protrusion 44 at a side of the end nut 14. The end nut 14 having an inner thread that is connectable to the inner screw 12. The inner screw 12 can be rotated so as to draw the end nut 14 towards the proximal end 30 of the inner screw 12. Also, the end nut 44 has a first end 40 and a second end 42. The second end 42 has a diameter 41 greater than a diameter 43 of the first end 40. For instance, as illustrated best in FIG. 1, the end nut 44 is a truncated cone shape.

Figure 2B:
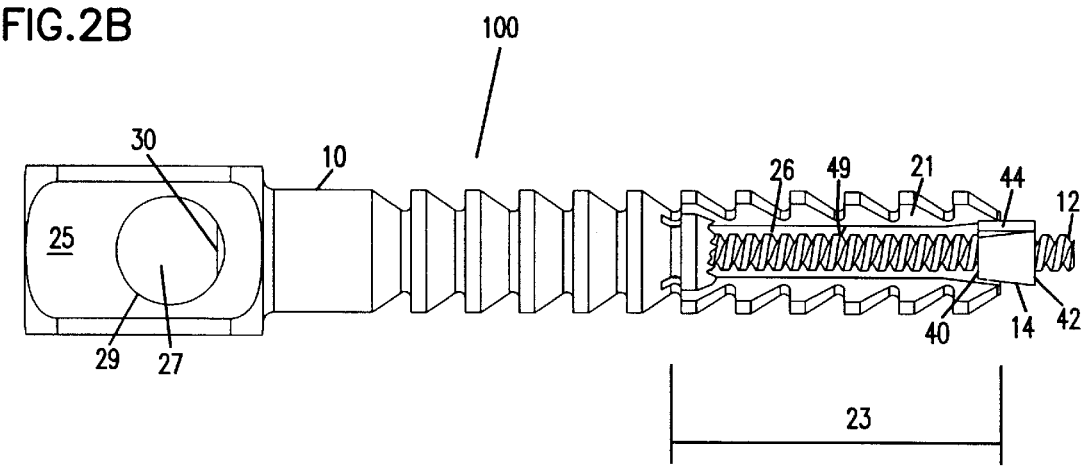
FIG. 2B represents a partial cross-sectional view of the expandable screw apparatus of FIG. 1 showing an end nut before engagement with longitudinal slits of an outer screw of the expandable screw apparatus in accordance with the principles of the present invention.
Figure 2C:
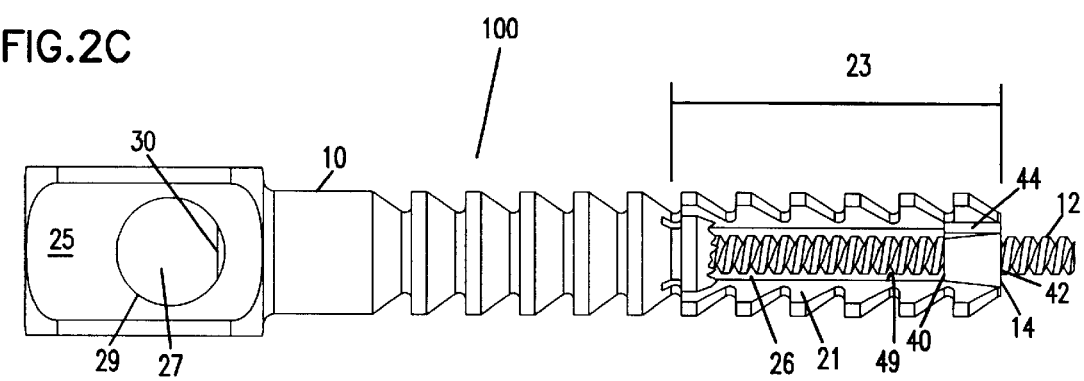
FIG. 2C represents a partial cross-sectional view of the expandable screw apparatus of FIG. 1 showing the end nut engaged with the longitudinal slits.
Figure 2D:
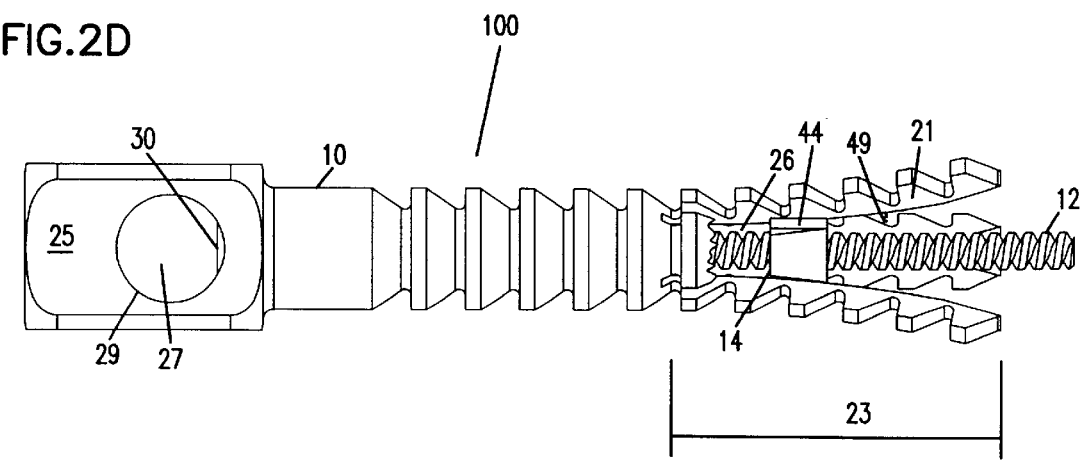
FIG. 2D represents a partial cross-sectional view of the expandable screw of FIG. 1 showing the end nut drawn into the outer screw and showing the expandable screw apparatus expanded.

In FIGS. 2D and 3A, B, the expandable screw apparatus 100 is shown in its expanded state. In FIG. 2C (also in FIG. 4), prior to expansion of the outer screw 10, the end nut 14 is shown engaged into the longitudinal slits 21 of the outer screw 10. In FIGS. 2D and 3A, B, the diameter of the outer screw 10 along the longitudinal slit length 23 is illustrated as greater than the diameter of at least the remaining threaded portion of the outer screw 10, due to expansion of the outer screw 10 of the screw apparatus 100. It is best shown in FIG. 2D where the end nut 14 has been drawn in towards the proximal end 30 of the inner screw 12. The second diameter 41 of the end nut 14 is greater than the diameter 24 of the longitudinal hollow core 26, but the first diameter 43 of the end nut 14 is less than the diameter 24 of the hollow core 26. This provides a structure for the end nut 14 to be moved into the hollow core 26 as it is drawn in with the inner screw 12, thereby pushing on the walls of the longitudinal slits 21 outwardly, which expands gaps 90 between the longitudinal slits 21. Furthermore, the tapered portion 39 of the outer screw 10 engages with the outer surface of the end nut 14, and the lip protrusion 44 is received in one of the gaps 90 between the longitudinal slits 21. The expandable screw apparatus can be made of an appropriate material such as, but not limited to, a metal alloy, stainless steel, etc.

The present invention further provides a driving and expanding assembly 99 for the expandable screw apparatus 100.

Figure 4:
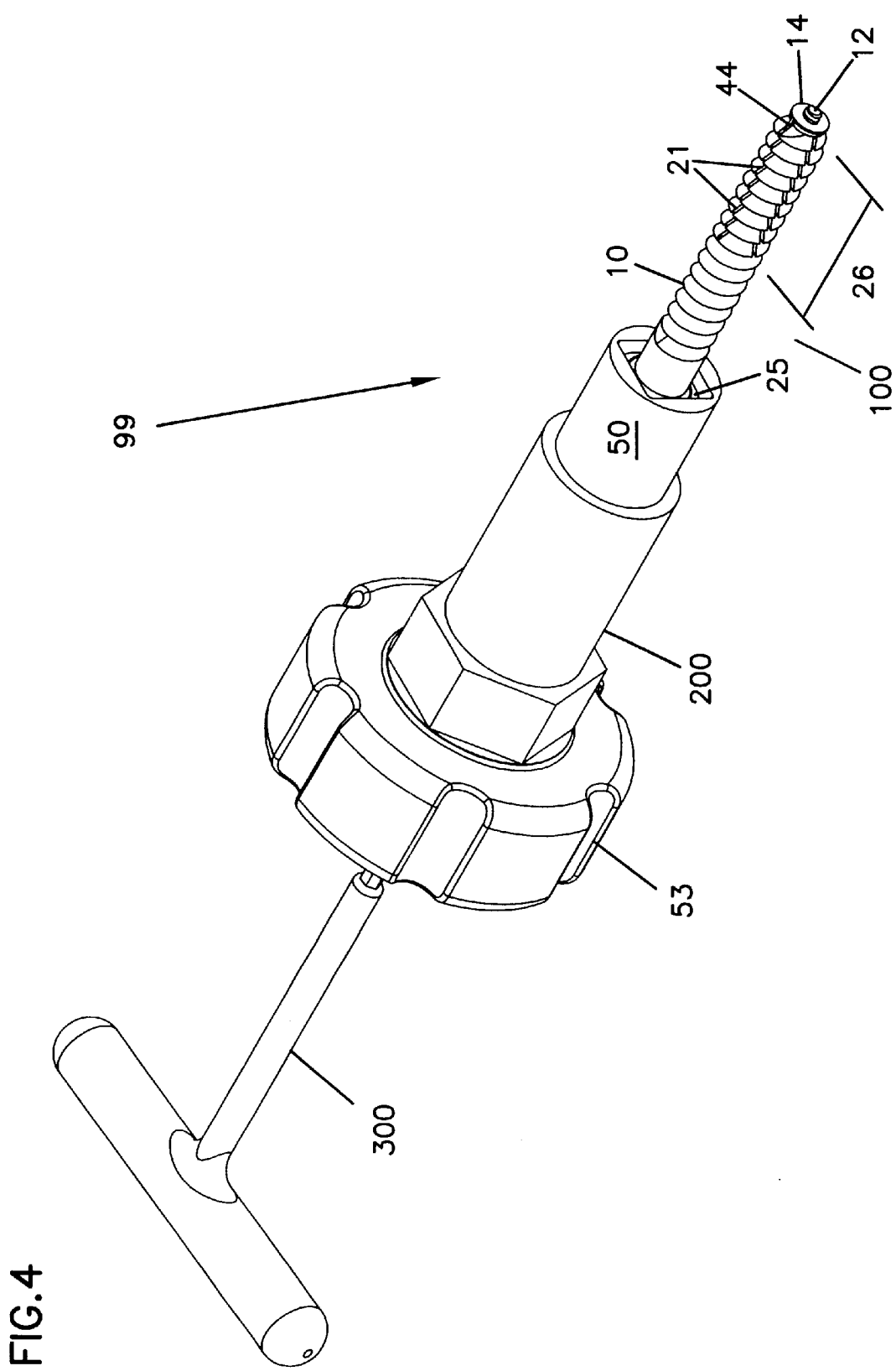
FIG. 4 represents a perspective view of one embodiment of a driving and expanding assembly for an expandable screw apparatus in accordance with the principles of the present invention.
Figure 5:
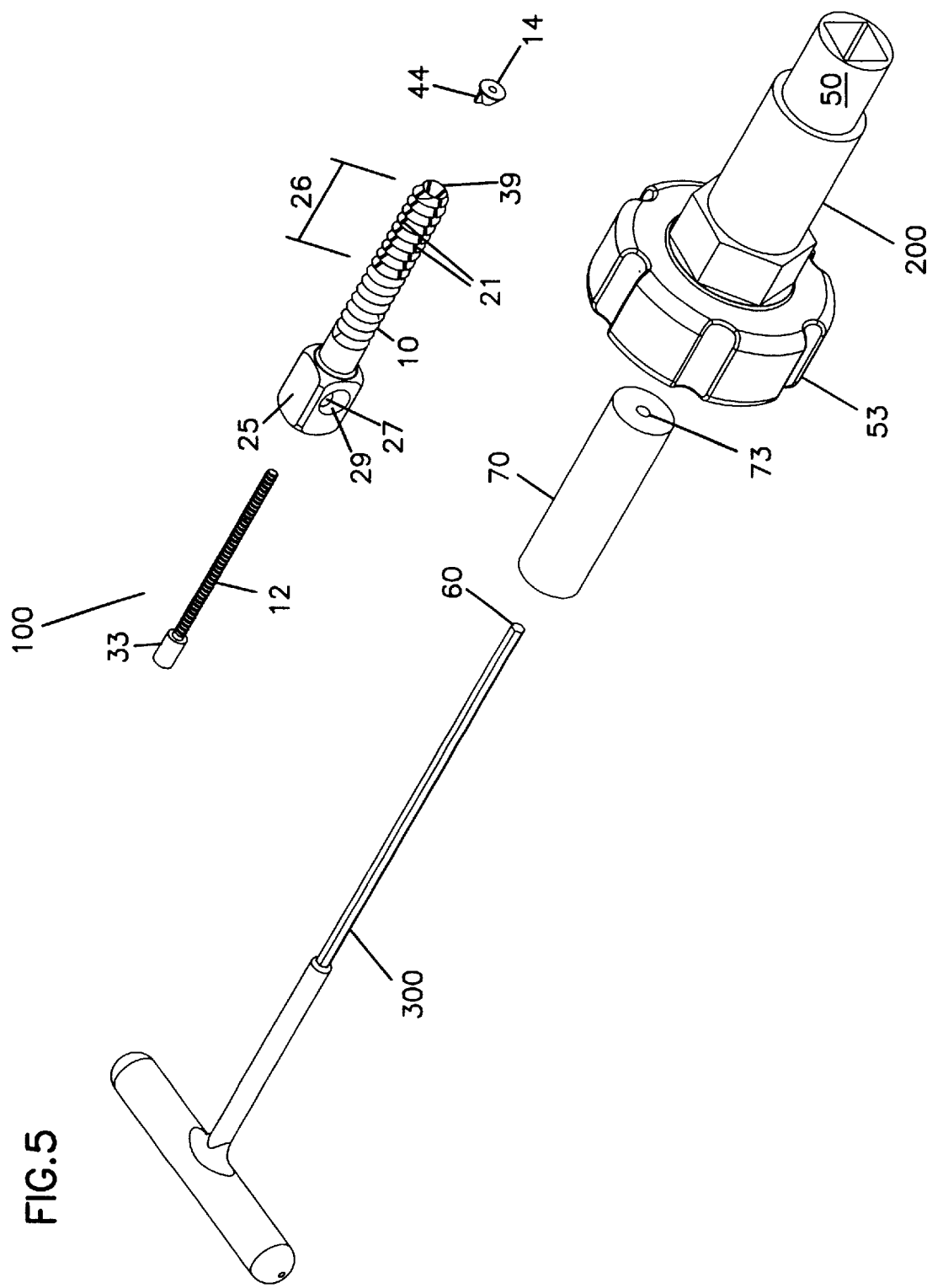
FIG. 5 represents an exploded view of the driving and expanding assembly for an expandable screw apparatus in FIG. 4.
Figure 6A:
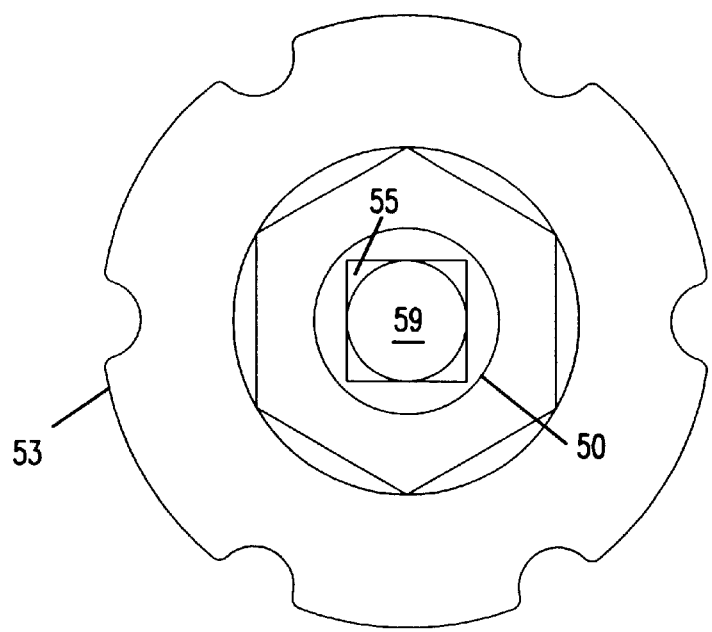
FIG. 6A represents an elevational front view of a distal end of a driver mechanism of the driving and expanding assembly for an expandable screw in FIG. 4.
Figure 6B:
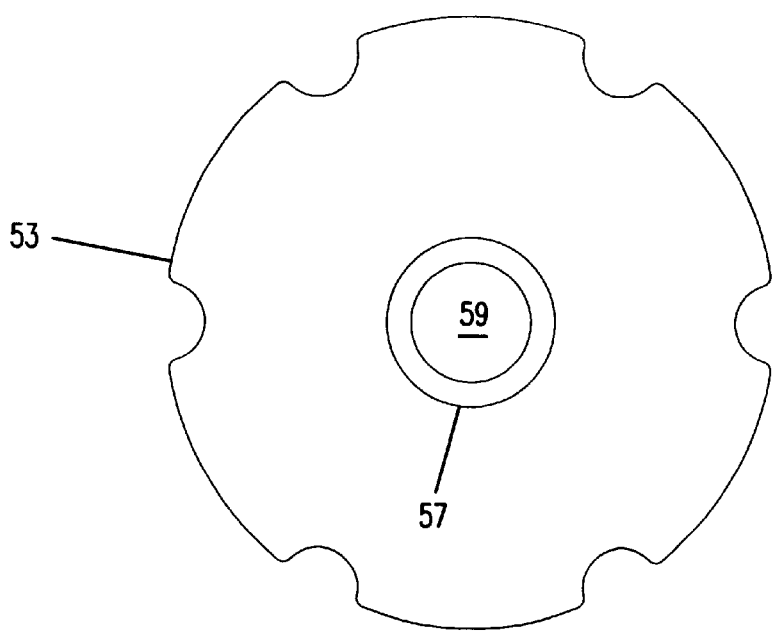
FIG. 6B represents a rear view of a proximal end of the driver mechanism of the driving and expanding assembly for an expandable screw in FIG. 4.

FIGS. 4 and 5 illustrate one embodiment of the assembly 99. The assembly 99 includes the expandable screw apparatus 100 previously described above in FIGS. 1–3, a driver mechanism 200, and an elongated stabilizing member 300. The driver mechanism 200 includes a knob 53 for rotating and actuating the driver mechanism 200, and a structural end 50 configured to receive the structural head 25 of the outer screw 10. In FIGS. 6A and 6B, a first inner stop 55 inside of the structural head 50 provides for limited insertion of the structural head 25. Furthermore, the driver mechanism 200 is provided with a hollow shaft 59 extending in a longitudinal direction along the central axis of the driver mechanism 200.

In FIG. 5, the elongated stabilizing member 300 has an end 60, which is insertable first through the hollow shaft 59, shown in FIGS. 6A, B of the driver mechanism 200 at the proximal end 20 of the outer screw 10 and through the hole region 27, and fit to the insertion space 35 of the proximal end cap 33 of the inner screw 12 (as shown in FIG. 2A). Further, an elongated centering member 70 is provided that is insertable through the hollow shaft 59 of the driving mechanism 200 to a second inner stop 57 disposed before the distal head 50 inside of the driving mechanism 200. The centering member 70 has a longitudinal through hole 73 along the longitudinal central axis allowing the elongated stabilizing member 300 to be positioned such that it connects and fits with the insertion space 35 of the inner screw 12. The centering member 70 is cylindrical in shape. Moreover, the end 60 of the stabilizing member end 60, while being connected to the inner screw 12, provides means for moving the end nut 14 inside the longitudinal slits 21 of the outer screw 10. The stabilizing member 300 is preferably a T-handle Allen Wrench as shown in FIG. 4.

As shown in its assembled form in FIG. 4, the assembly 99 dynamically expands an expandable screw by simultaneously providing both driving and expanding motions for fixation of the screw apparatus 100 to a structure (see later in FIGS. 7A, B and C). Insertion of the expandable screw apparatus 100 into a structure a certain length can be achieved with the driver mechanism 200 by turning the knob 53 to actuate the driver mechanism 200. No expansion of the screw apparatus 100 is occurring at this point. Simultaneous driving and expanding, i.e. the dynamic expansion, occurs when the end nut 14 is engaged with one of the longitudinal slits 21, where the end nut 14 engages with the tapered portion 39 of the distal end 22 of the outer screw 10, and the protrusion lip 44 is retained in one of the gaps 90 between the longitudinal slits 21. Simultaneous driving and expanding is realized by continuous driving of the screw apparatus 100 into a structure, such as but not limited to bone, while holding the stabilizing member 300, which is engaged in the insertion space 35 of the end cap 33 of the inner screw 12. This simultaneous driving and expanding achieves a dynamic expansion of the screw apparatus 100 where the screw apparatus 100 is being driven in and expanded at the same time. Holding the stabilizing member 300 and actuating the driver mechanism 200 allow the end nut 14 to be drawn inwardly toward the proximal ends 22 and 30 of the outer screw 10 and inner screw 12, respectively. Further, with the lip protrusion 44 of the end nut 14 engaged with one of the gaps 90 between the longitudinal slits 21, rotation of the outer screw 10, by the knob 53 and simultaneous holding of the inner screw 12 by the stabilizing member 300, the end nut 14 is drawn inwardly. This relative movement of the inner screw 12 and outer screw 10 allows the end nut 14 to expand the screw apparatus 100 as the second diameter 41 of the end nut 14 is greater than the hollow core diameter 24. When the end nut 14 is drawn inwardly a force pushes against the inner walls 49 of the outer screw 10 of the screw apparatus 100 causing expansion.

In another embodiment of driving and expanding the expandable screw apparatus 100, the end nut 14 may not be engaged to one of the gaps 90 between the longitudinal slits 21. In this event, after insertion of the screw apparatus 100 a length into a structure, the stabilizing member 300 is rotated to draw the end nut 14 towards and into one of the gaps 90 of the longitudinal slits 21 so as to engage the end nut 14. Thereafter, the expandable screw apparatus 100 is dynamically expanded by incorporating similar procedural steps above.

Figure 7A:
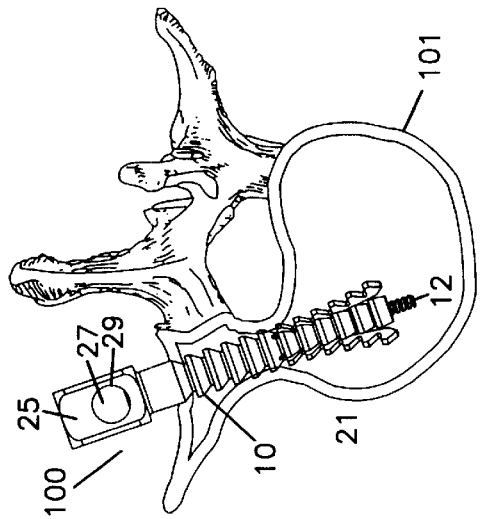
FIG. 7A represents a side view of the expandable screw apparatus of FIG. 1 driven into a structure.
Figure 7B:
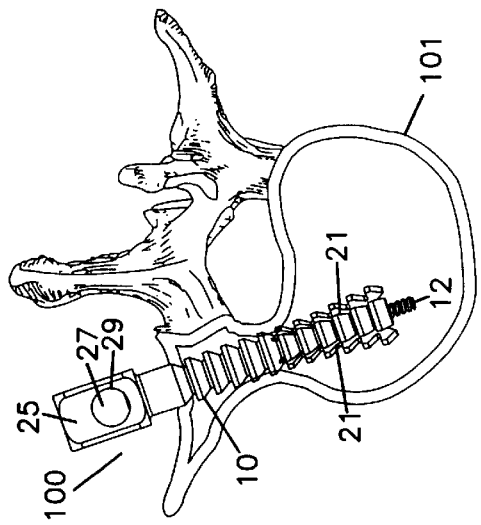
FIG. 7B represents a side view of the expandable screw apparatus of FIG. 1 driven into and partially expanded in the structure of FIG. 7A in accordance with the principles of the present invention.
Figure 7C:
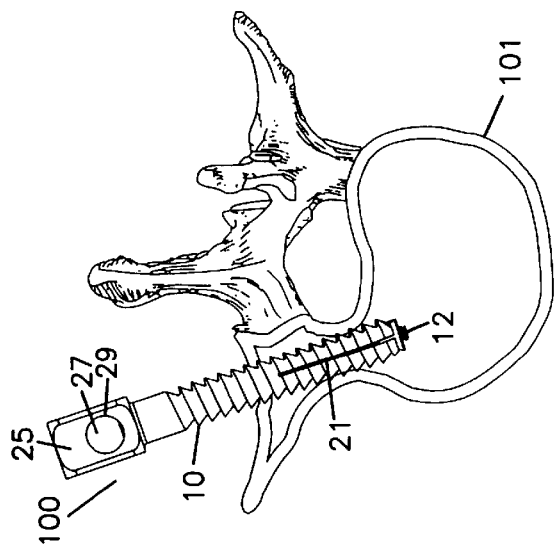
FIG. 7C represents a side view of the expandable screw apparatus of FIG. 1 driven into and expanded in the structure of FIG. 7A in accordance with the principles of the present invention.

In FIGS. 7A–C, the expandable screw apparatus 100 is driven into a structure 101, such as a bone structure. FIG. 7A illustrates that the expandable screw apparatus 100 is in its non-expanded state. FIG. 7B illustrates that the expandable screw apparatus 100 is in its partially expanded state. FIG. 7C illustrates that the expandable screw apparatus 100 is in a final expanded state. Reference numerals referring to features of the expandable screw apparatus in FIGS. 7A–C have been mentioned in detail in preceding FIGS. 1–6, and need no further description.

In addition to the above advantages of improved holding power and operation convenience, other advantages can be realized with respect to the present invention. Dynamic expansion of an expandable screw according to the present invention can allow for a safer and easier way in the fixation of screws into a structure. For instance, the simultaneous driving and expanding of an expandable screw places less pressure on a cutting surface between the screw and the structure, for example, in a bone surface, especially in the event the bone environment is hard. The existing methods use a static expansion technique, i.e. expanding a screw after the full insertion of the screw, which would apply high pressure on the cutting surface. Static expansion often causes damage to the screw and/or the structures. Dynamic expansion of the present invention allows the force to be distributed during the course of insertion. Also, the assembly of the present invention provides more controls for expansion allowing structural variability to be made not only to the inner and outer screws, but also to the end nut.

Having described the embodiments of the present invention, modifications and equivalents may occur to one skilled in the art. It is intended that such modifications and equivalents shall be included with the scope of the claims, which are appended hereto.

We claim:

1. An expandable screw apparatus, comprising:
    an outer screw having a longitudinal hollow core and a plurality of longitudinal expandable slits proximate a distal end;
    an inner screw, disposed inside the longitudinal hollow core of the outer screw, having a distal end extended outside the longitudinal hollow core of the outer screw; said inner screw is threaded with one of a right handed orientation or a left handed orientation on an outer surface, and having opposite orientation to an outer surface of said outer screw; and
    an end nut, engaged with the distal end of the inner screw, wherein by rotating the outer screw relative to the inner screw while simultaneously holding the inner screw, the end nut is drawn into the hollow core of the outer screw, thereby causing simultaneous expansion of the expandable slits in a transversal direction.

2. The expandable screw apparatus of claim 1, further comprising a driver mechanism, wherein the driver mechanism includes a first driver which drives the outer screw and a second driver which drives the inner screw.

3. An expandable screw apparatus according to claim 1, wherein said longitudinal hollow core of said outer screw comprises a smooth surface.

4. An expandable screw apparatus according to claim 2, wherein a proximal end of said outer screw comprises a structural head for attachment to said first driver and having a longitudinal hole region in a longitudinal direction towards a stop region.

5. An expandable screw apparatus according to claim 4, wherein said structural head comprises through holes for support of a structural frame, said through holes are in a direction transverse to said longitudinal hole region of said structural head.

6. An expandable screw apparatus according to claim 1, wherein said longitudinal expandable slits comprise silts spaced 90° apart.

7. An expandable screw apparatus according to claim 1, wherein said outer screw is threaded wit one of a right handed orientation or a left handed orientation on an outer surface.

8. An expandable screw apparatus according to claim 1, wherein said inner screw includes a proximal end, said proximal end including a proximal end cap wit a diameter greater than a diameter of a remaining portion of said inner screw and a diameter of said longitudinal hollow core, said inner screw is insertable through a proximal end of said outer screw and said longitudinal hollow core of said outer screw towards said distal end of said outer screw to a point where said proximal end cap contacts a stop region of said outer screw.

9. An expandable screw apparatus according to claim 8, wherein said proximal end cap of said inner screw has a diameter less than a diameter of said longitudinal hole region of said outer screw.

10. An expandable screw apparatus according to claim 8, wherein said proximal end cap comprises an insertion space allowing connection to a stabilizing member.

11. An expandable screw apparatus according to claim 1, wherein said end nut comprises a lip protrusion on a side surface of said end nut.

12. An expandable screw apparatus according to claim 1, wherein said end nut comprises a first end and a second end where said first end includes a first diameter less than a second diameter of said second end.

13. An expandable screw apparatus according to claim 12, wherein said end nut is a truncated conical shape.

14. A driving and expanding assembly comprising:
    an expandable screw apparatus including an outer screw having a longitudinal hallow core and a plurality of longitudinal expandable slits proximate a distal end;
    an inner screw, disposed inside the longitudinal hollow core of the outer screw, having a distal end extended outside the longitudinal hollow core of the outer strew; said inner screw is threaded with one of a right handed orientation or a left handed orientation and on an outer surface and having opposite orientation of an outer surface of said outer screw; and
    an end nut, engaged with the distal end of the inner strew, wherein by rotating the outer screw relative to the inner screw while simultaneously holding the inner screw, the end nut is drawn into the hollow core of the outer screw, thereby causing simultaneous expansion of the expandable slits in a transversal direction;
    a driver mechanism with a structural end connectable to a structural head of said outer screw, said driver having a hollow shaft; and
    an elongated stabilizing member including an end insertable first through said hollow shaft of said driver mechanism towards a proximal end of said outer screw and through a hole region of said outer screw, said elongated stabilizing member being connectable to an insertion space of a proximal end cap of said inner screw.

15. A driving and expanding assembly according to claim 14, wherein a surface of said longitudinal hollow core of said outer screw comprises a smooth surface.

16. A driving and expanding assembly according to claim 14, wherein said structural head comprises through holes for support of a structural frame, said through holes are in a direction transverse to said longitudinal hole region of said structural head.

17. A driving and expanding assembly according to claim 14 wherein said longitudinal slits comprises slits spaced 90° span.

18. A driving and expanding assembly according to claim 14 wherein said outer screw is threaded wit one of a right handed orientation or a left handed orientation.

19. A driving and expanding assembly according to claim 14 wherein said end nut comprises a first end and a second end where said first end includes a first diameter less than a second diameter of said second end.

20. A driving and expanding assembly according to claim 19 wherein said end nut is a truncated conical shape.

21. A driving and expanding assembly according to claim 14, wherein said elongated stabilizing member is a T-handle allen wrench.

22. A driving and expanding assembly according to claim 14, comprising an elongated centering member insertable into said hollow shaft of said driving mechanism to a second inner stop before said distal head of said driving mechanism, said elongated centering member having a longitudinal through hole allowing centering of said elongated stabilizing member to be connected to said insertion space of said inner screw.

23. A driving and expanding assembly according to claim 22, wherein said elongated centering member is a cylindrical shape.

* * * * *

UNITED STATES PATENT AND TRADEMARK OFFICE
CERTIFICATE OF CORRECTION

PATENT NO. : 6,668,688 B2
DATED : December 30, 2003
INVENTOR(S) : Zhao et al.

It is certified that error appears in the above-identified patent and that said Letters Patent is hereby corrected as shown below:

<u>Title page,</u>
Insert item:
-- [73]  Assignee: Mayo Foundation for Medical Education and Research --

Signed and Sealed this

Twentieth Day of April, 2004

JON W. DUDAS
*Acting Director of the United States Patent and Trademark Office*